United States Patent
Loeker et al.

(10) Patent No.: US 8,906,824 B2
(45) Date of Patent: Dec. 9, 2014

(54) WATER-ABSORBING POLYMER STRUCTURES PRODUCED USING POLYMER DISPERSIONS

(75) Inventors: Frank Loeker, Krefeld (DE); Heinz Bremus, Krefeld (DE); Rüdiger Gerlach, Mülheim (DE); Scott J. Smith, Greensboro, NC (US)

(73) Assignee: Evonik Degussa GmbH, Essen (DE)

( * ) Notice: Subject to any disclaimer, the term of this patent is extended or adjusted under 35 U.S.C. 154(b) by 634 days.

(21) Appl. No.: 12/516,745

(22) PCT Filed: Dec. 18, 2007

(86) PCT No.: PCT/EP2007/011093
§ 371 (c)(1),
(2), (4) Date: Sep. 4, 2009

(87) PCT Pub. No.: WO2008/074456
PCT Pub. Date: Jun. 26, 2008

(65) Prior Publication Data
US 2010/0075844 A1   Mar. 25, 2010

(30) Foreign Application Priority Data
Dec. 18, 2006   (DE) .................. 10 2006 060 156

(51) Int. Cl.
*B01J 20/26* (2006.01)
*C08F 2/10* (2006.01)
(Continued)

(52) U.S. Cl.
CPC . *C08F 2/10* (2013.01); *A61L 15/60* (2013.01); *C08F 220/06* (2013.01); *C08J 3/245* (2013.01); *C08L 31/04* (2013.01); *C08L 33/02* (2013.01); *C08L 33/08* (2013.01); *C08L 35/06* (2013.01); *C08L 220/40* (2013.01); *C08F 222/1006* (2013.01); *C08J 2333/02* (2013.01)
USPC ......................................................... 502/402

(58) Field of Classification Search
CPC ....................................................... A61L 15/60
USPC ........................................... 524/832; 502/402
See application file for complete search history.

(56) References Cited

U.S. PATENT DOCUMENTS

| 4,076,663 A | 2/1978 | Masuda et al. |
| 4,131,576 A | 12/1978 | Iovine et al. |

(Continued)

FOREIGN PATENT DOCUMENTS

| DE | 2706135 A1 | 8/1978 |
| DE | 2840010 A1 | 6/1979 |

(Continued)

OTHER PUBLICATIONS
Reference: Polymer Properties. Obtained from www.sigmaaldrich.com. No Author, No Date.*
(Continued)

*Primary Examiner* — Michael Pepitone
*Assistant Examiner* — Michael A Salvitti
(74) *Attorney, Agent, or Firm* — Smith Moore Leatherwood LLP; Philip P. McCann; John P. Zimmer

(57) ABSTRACT

The present invention relates to a process for the production of water-absorbing polymer structures, comprising the process steps of providing of an aqueous monomer solution comprising a polymerizable, monoethylenically unsaturated monomer ($\alpha 1$) carrying acid groups or a salt thereof; free-radical polymerization of the aqueous monomer solution to give a polymer gel, drying of the optionally comminuted polymer gel to give water-absorbing polymer structures, and surface post-crosslinking of the optionally ground and sieved water-absorbing polymer structures, wherein a thermoplastic polymer is added to the aqueous monomer solution before process step ii) or during process step ii), preferably before process step ii), or II) the polymer gel after process step ii) and before process step iv) or during process step iv), preferably before process step iv), or III) the water-absorbing polymer structure after process step iv).

9 Claims, 1 Drawing Sheet

Amount of Lurapret D313 [%]

(51) Int. Cl.
*A61L 15/60* (2006.01)
*C08F 220/06* (2006.01)
*C08J 3/24* (2006.01)
*C08L 31/04* (2006.01)
*C08L 33/02* (2006.01)
*C08L 33/08* (2006.01)
*C08L 35/06* (2006.01)
*C08F 222/10* (2006.01)

(56) References Cited

U.S. PATENT DOCUMENTS

| | | | |
|---|---|---|---|
| 4,179,367 A | 12/1979 | Barthell et al. | |
| 4,286,082 A | 8/1981 | Tsubakimoto et al. | |
| 4,340,706 A | 7/1982 | Obayashi et al. | |
| 4,587,308 A | 5/1986 | Makita et al. | |
| 4,647,617 A * | 3/1987 | Saotome | 524/733 |
| 5,032,628 A | 7/1991 | Choi et al. | |
| 5,314,420 A | 5/1994 | Smith et al. | |
| 5,378,528 A * | 1/1995 | Makoui | 428/219 |
| 5,399,591 A | 3/1995 | Smith et al. | |
| 5,409,771 A | 4/1995 | Dahmen et al. | |
| 5,451,613 A | 9/1995 | Smith et al. | |
| 5,462,972 A | 10/1995 | Smith et al. | |
| 5,610,220 A | 3/1997 | Klimmek et al. | |
| 5,672,633 A | 9/1997 | Brehm et al. | |
| 5,712,316 A | 1/1998 | Dahmen et al. | |
| 5,731,365 A | 3/1998 | Engelhardt et al. | |
| 6,060,557 A | 5/2000 | Dahmen et al. | |
| 6,124,391 A | 9/2000 | Sun et al. | |
| 6,353,148 B1 * | 3/2002 | Gross | 604/368 |
| 6,387,495 B1 | 5/2002 | Reeves et al. | |
| 6,403,700 B1 | 6/2002 | Dahmen et al. | |
| 6,716,894 B2 | 4/2004 | Kajikawa et al. | |
| 6,906,131 B2 | 6/2005 | Ahmed et al. | |
| 7,157,141 B2 | 1/2007 | Inger et al. | |
| 7,163,969 B2 | 1/2007 | Ahmed et al. | |
| 7,169,843 B2 | 1/2007 | Smith et al. | |
| 7,173,086 B2 | 2/2007 | Smith et al. | |
| 7,241,820 B2 | 7/2007 | Smith et al. | |
| 7,285,614 B2 | 10/2007 | Jonas et al. | |
| 7,291,674 B2 | 11/2007 | Kang et al. | |
| 7,312,286 B2 | 12/2007 | Lang et al. | |
| 7,335,713 B2 | 2/2008 | Lang et al. | |
| 7,399,813 B2 | 7/2008 | Lang et al. | |
| 7,482,058 B2 | 1/2009 | Ahmed et al. | |
| 7,488,541 B2 | 2/2009 | Ahmed et al. | |
| 7,507,475 B2 * | 3/2009 | Inger et al. | 428/403 |
| 7,541,395 B2 | 6/2009 | Reimann et al. | |
| 7,612,016 B2 * | 11/2009 | Mertens et al. | 502/439 |
| 7,842,386 B2 * | 11/2010 | Loeker et al. | 428/407 |
| 8,247,499 B2 * | 8/2012 | Walden et al. | 525/330.2 |
| 2002/0039869 A1 * | 4/2002 | Achille | 442/417 |
| 2003/0111774 A1 * | 6/2003 | Kellenberger et al. | 264/518 |
| 2003/0113463 A1 * | 6/2003 | Ko et al. | 427/402 |
| 2003/0181115 A1 | 9/2003 | Nagasuna et al. | |
| 2004/0071966 A1 * | 4/2004 | Inger et al. | 428/394 |
| 2004/0110897 A1 * | 6/2004 | Sakamoto et al. | 524/832 |
| 2005/0054784 A1 * | 3/2005 | Qin et al. | 525/329.4 |
| 2005/0096435 A1 * | 5/2005 | Smith et al. | 525/244 |
| 2005/0096453 A1 | 5/2005 | Flynn et al. | |
| 2005/0256469 A1 | 11/2005 | Qin et al. | |
| 2006/0029782 A1 | 2/2006 | Harren et al. | |
| 2006/0173097 A1 | 8/2006 | Ahmed et al. | |
| 2007/0066718 A1 | 3/2007 | Smith et al. | |
| 2007/0066754 A1 * | 3/2007 | Loeker et al. | 525/127 |
| 2007/0129515 A1 * | 6/2007 | Lang et al. | 526/218.1 |
| 2007/0135554 A1 | 6/2007 | McIntosh et al. | |
| 2007/0135785 A1 | 6/2007 | Qin et al. | |
| 2007/0167560 A1 | 7/2007 | Smith et al. | |
| 2008/0021130 A1 | 1/2008 | McIntosh et al. | |
| 2008/0234420 A1 | 9/2008 | Smith et al. | |
| 2010/0075844 A1 * | 3/2010 | Loeker et al. | 502/402 |
| 2012/0271260 A1 * | 10/2012 | Azad et al. | 604/359 |

FOREIGN PATENT DOCUMENTS

| | | |
|---|---|---|
| DE | 3503458 A1 | 8/1985 |
| DE | 3713601 A1 | 11/1988 |
| DE | 4020780 C1 | 8/1991 |
| DE | 4244548 A1 | 7/1994 |
| DE | 4418818 A1 | 1/1995 |
| DE | 4333056 A1 | 3/1995 |
| DE | 19529348 A1 | 2/1997 |
| DE | 10334286 A | 3/2005 |
| EP | 0388120 A1 | 9/1990 |
| EP | 612533 A1 | 8/1994 |
| EP | 827753 A2 | 3/1998 |
| JP | 2001220415 A | 8/2001 |
| WO | 91/08042 A1 | 11/1991 |
| WO | 95/11932 A1 | 5/1995 |
| WO | 96/05234 A1 | 2/1996 |
| WO | 99/34843 A1 | 7/1999 |
| WO | 01/74913 A1 | 10/2001 |
| WO | 02/56812 A1 | 7/2002 |
| WO | 2004/037903 A2 | 5/2004 |
| WO | 2005/011860 A2 | 2/2005 |
| WO | 2005/044900 A1 | 5/2005 |
| WO | 2007/070262 A2 | 6/2007 |
| WO | 2007/070776 A2 | 6/2007 |
| WO | 2008/074456 A2 | 6/2008 |

OTHER PUBLICATIONS

U.S. Appl. No. 10/699,205 NonFinal Rejection Sep. 13, 2005.
U.S. Appl. No. 10/699,205 NonFinal Rejection Mar. 1, 2006.
Ahmed et al., U.S. Appl. No. 11/778,372, filed Jul. 16, 2007.
Frank et al., U.S. Appl. No. 11/570,849, filed Aug. 6, 2007.
International Preliminary Report on Patentability mailed on Jul. 9, 2009 in PCT/EP2007/011093.
International Search Report mailed on Jun. 27, 2009 in PCT/EP2007/011093.
Smith et al., U.S. Appl. No. 11/766,399, filed Jun. 21, 2007.

* cited by examiner

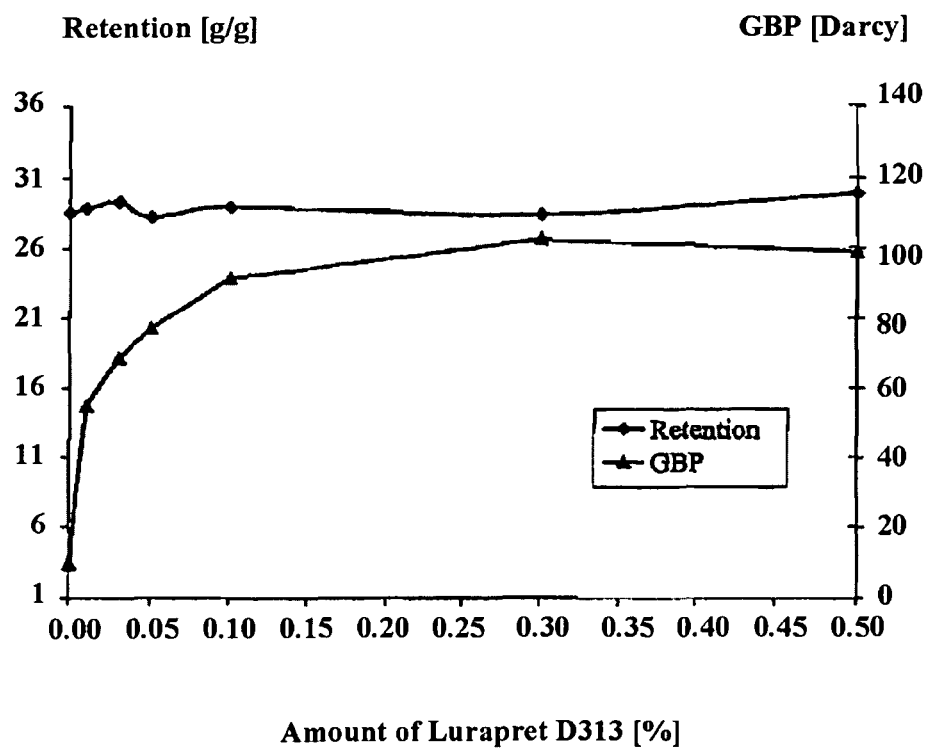

WATER-ABSORBING POLYMER STRUCTURES PRODUCED USING POLYMER DISPERSIONS

This application is a national stage application under 35 U.S.C. 371 of international application No. PCT/EP2007/011093 filed 18 Dec. 2007, and claims priority to German Application No. DE 10 2006 060 156.4 filed 18 Dec. 2006, the disclosures of which are expressly incorporated herein by reference.

BACKGROUND

The present invention relates to a process for the production of water-absorbing polymer structures. The invention also relates to the water-absorbing polymer structures obtainable by this process, water-absorbing polymer structures, a composite material, a process for the production of a composite material, the composite material obtainable by this process, chemical products, such as foams, shaped articles, fibers, foils, films, cables, sealing materials, liquid-absorbing hygiene articles, carriers for plant and fungal growth-regulating agents, packaging materials, soil additives or building materials, the use of water-absorbing polymer structures and the use of thermoplastic polymers.

Superabsorbers are water-insoluble, crosslinked polymers which are capable, by swelling and formation of hydrogels, of taking up large amounts of water, aqueous liquids, in particular body fluids, preferably urine or blood, and retaining these under pressure. Superabsorbers preferably absorb at least 100 times their own weight of water. Further details on superabsorbers are disclosed in "Modern Superabsorbent Polymer technology", F. L. Buchholz, A. T. Graham, Wiley-VCH, 1998". As a result of these characteristic properties, these water-absorbing polymers are chiefly incorporated into sanitary articles, such as, for example, babies' diapers, incontinence products or sanitary towels.

The superabsorbers currently commercially available are essentially crosslinked polyacrylic acids or crosslinked starch-acrylic acid graft polymers, in which some of the carboxyl groups are neutralized with sodium hydroxide solution or potassium hydroxide solution. These are obtainable by subjecting monomeric acrylic acid or salts thereof to free-radical polymerization in the presence of suitable crosslinking agents. In this context, various polymerization processes can be used, such as, for example, solution polymerization, emulsion polymerization or suspension polymerization. In the end, water-absorbing polymers in particulate form having a particle diameter in a range of from 150 to 850 µm are obtained by these various processes, and are then incorporated into the sanitary articles.

In order to improve the absorbency and swellability of these water-absorbing polymer particles, numerous processes have been described in which the surface of the polymer particles is modified. It is thus known, for example, from DE 40 20 780 C1 to react the water-absorbing polymer particles with alkylene carbonates, which can react with the carboxyl groups of the polymer particles. The surface post-crosslinking affected in this manner leads to an increase in the absorption of the polymers under the action of a pressure.

In addition to the reaction of the polymer composition with reactive compounds, numerous processes with which the properties of the water-absorbing polymer particles, in particular the permeability thereof, can be achieved by a coating with inorganic or organic fine particles are also described in the prior art.

Thus, DE 35 03 458 A1 describes that the absorption capacity, the rate of absorption and the gel strength of super-absorber particles can be improved by application of inert inorganic powder materials, such as, for example, silicon dioxide, in the presence of post-crosslinking agents.

To reduce the hygroscopicity and therefore to reduce the caking of the polymer particles, EP 0 388 120 A1 proposes coating the polymer particles with a porous powder of highly pure silicon dioxide, the powder having an average particles size of from 0.1 to 30 µm and a specific surface area of 500 $m^2/g$.

However, all these processes for subsequent modification have the common feature that they lead to a release of fine particles in the form of dust, these fine particles being formed by mechanical stress, such as, for example, by pneumatic conveying and the resultant abrasion of the water-absorbing polymer particles. In addition to the associated dust pollution, a further disadvantage in the use of inorganic fine particles for surface modification of water-absorbing polymer structures lies in that fact that if these inorganic fine particles are employed during the surface crosslinking in particular, the current uptake of the post-crosslinking reaction can be comparatively high.

The present invention was based on the object of overcoming the disadvantages emerging from the prior art.

In particular, the present invention was based on the object of providing water-absorbing polymer structures which show comparatively low formation of dust and furthermore can be employed in hygiene articles, even in a high concentration, without the so-called "gel blocking" phenomenon occurring. The water-absorbing polymer structures should moreover be as easy as possible to meter in a device for the production of hygiene articles.

The present invention was also based on the object of providing a process for the production of water-absorbing polymer structures having the properties described above, which can also be carried out without the use of finely divided inorganic particles.

SUMMARY

The present invention includes various embodiments set forth in the claims and including the following as taken in context with the present invention:

A contribution to achieving the abovementioned objects is made by a process for the production of water-absorbing polymer structures, comprising the process steps:
i) provision of an aqueous monomer solution containing
a polymerizable, monoethylenically unsaturated monomer (α1) carrying acid groups or a salt thereof or a polymerizable, monoethylenically unsaturated monomer containing a protonated or quaternized nitrogen, or a mixture of these monomers, a polymerizable, monoethylenically unsaturated monomer carrying acid groups being particularly preferred and acrylic acid being most preferred,
optionally a monoethylenically unsaturated monomers (α2) which can be polymerized with the monomer (α1), and
optionally a crosslinking agent (α3),
ii) free-radical polymerization of the aqueous monomer solution to give a polymer gel,
iii) optionally comminution of the polymer gel,
iv) drying of the optionally comminuted polymer gel to give water-absorbing polymer structures,
v) optionally grinding and sieving of the water-absorbing polymer structures and vi) surface post-crosslinking of the optionally ground and sieved water-absorbing polymer structures,
wherein
a thermoplastic polymer is added to
I) the aqueous monomer solution before process step ii) or during process step ii), preferably before process step ii),
II) the polymer gel after process step ii) and before process step iv) or during process step iv), preferably before process step iv), or
III) the water-absorbing polymer structure after process step iv).

FIGURES

The foregoing and other features, aspects, and advantages of the present invention will become better understood with regard to the following description, appended claims, and accompanying drawings where:
FIG. 1 is a chart showing graphs of retention and GBP properties based on amount of Lurapret D313.

DETAILED DESCRIPTION

Polymer structures which are preferred according to the invention are fibers, foams or partides, fibers and particles being preferred and particles being particularly preferred.

Polymer fibers which are preferred according to the invention have dimensions such that they can be incorporated into or as yarns for textiles and also directly into textiles. It is preferable according to the invention for the polymer fibers to have a length in the range of from 1 to 500 mm, preferably 2 to 500 mm and particularly preferably 5 to 100 mm and a diameter in the range of from 1 to 200 denier, preferably 3 to 100 denier and particularly preferably 5 to 60 denier.

Polymer particles which are preferred according to the invention have dimensions such that they have an average particle size in accordance with ERT 420.2-02 in the range of from 10 to 3,000 μm, preferably 20 to 2,000 μm and particularly preferably 150 to 850 μm. In this context, it is particularly preferable for the content of polymer particles having a particle size in a range of from 300 to 600 μm to be at least 30 wt. %, particularly preferably at least 40 wt. % and most preferably at least 50 wt. %, based on the total weight of the post-crosslinked, water-absorbing polymer particles.

In process step i) of the process according to the invention, an aqueous monomer solution is first provided.

The monoethylenically unsaturated monomers (α1) carrying acid groups can be partly or completely, preferably partly neutralized. Preferably, the monoethylenically unsaturated monomers carrying acid groups are neutralized to the extent of at least 25 mol %, particularly preferably to the extent of at least 50 mol % and moreover preferably to the extent of 50-80 mol %. Reference is made in this connection to DE 195 29 348 A1, the disclosure of which is introduced herewith as reference. The neutralization can also take place partly or completely after the polymerization. Furthermore, the neutralization can be carried out with alkali metal hydroxides, alkaline earth metal hydroxides, ammonia and carbonates and bicarbonates. In addition, any further base which forms a water-soluble salt with the acid is conceivable. Mixed neutralization with various bases is also conceivable. Neutralization with ammonia and alkali metal hydroxides is preferred, particularly preferably with sodium hydroxide and with ammonia.

Furthermore, the free acid groups can predominate in a water-absorbing polymer structure obtainable by the process according to the invention, so that this polymer structure has a pH in the acid range. This acid water-absorbing polymer structure can be at least partly neutralized by a polymer structure having free basic groups, preferably amine groups, which is basic in comparison with the acid polymer structure. These polymer structures are called "mixed-bed ion exchange absorbent polymers" (MBIEA polymers) in the literature and are disclosed, inter alia, in WO 99/34843 A1. The disclosure of WO 99/34843 A1 is introduced herewith as reference and therefore forms part of the disclosure. As a rule, MBIEA polymers are a composition which comprises on the one hand basic polymer structures which are capable of exchanging anions, and on the other hand a polymer structure which is acid in comparison with the basic polymer structure and is capable of exchanging cations. The basic polymer structure contains basic groups and is typically obtained by polymerization of monomers (α1) which carry basic groups or groups which can be converted into basic groups. These monomers are above all those which contain primary, secondary or tertiary amines or the corresponding phosphines or at least two of the above functional groups. This group of monomers includes, in particular, ethyleneamine, allylamine, diallylamine, 4-aminobutene, alkyloxycyclins, vinylformamide, 5-aminopentene, carbodiimide, formal-dacin, melamine and the like, and secondary or tertiary amine derivatives thereof.

Preferred monoethylenically unsaturated monomers (α1) carrying acid groups are preferably those compounds which are mentioned as ethylenically unsaturated monomers (α1) containing acid groups in WO 2004/037903 A2, which is introduced herewith as reference and thus forms part of the disclosure. Particularly preferred monoethylenically unsaturated monomers (α1) carrying acid groups are acrylic acid and methacrylic acid, acrylic acid being most preferred.

Acrylamides, methacrylamides or vinylamides can be employed as monoethylenically unsaturated monomers (α2) which can be copolymerized with the monomers (α1).

Preferred (meth)acrylamides are, in addition to acrylamide and methacrylamide, alkyl-substituted (meth)acrylamides or aminoalkyl-substituted derivatives of (meth)acrylamide, such as N-methylol(meth)acrylamide, N,N-dimethylamino (meth)acrylamide, dimethyl-(meth)acrylamide or diethyl (meth)acrylamide. Possible vinylamides are, for example, N-vinylamides, N-vinylformamides, N-vinylacetamides, N-vinyl-N-methylacetamides, N-vinyl-N-methylformamides and vinylpyrrolidone. Among these monomers, acrylamide is particularly preferred.

Water-soluble monomers can be employed as monoethylenically unsaturated monomers (α2) which can be copolymerized with the monomers (α1). In this connection, alkoxypolyalkylene oxide(meth)acrylates, such as methoxypolyethylene glycol(meth)acrylates, are preferred in particular.

Water-dispersible monomers are furthermore conceivable as monoethylenically unsaturated monomers (α2) which can be copolymerized with the monomers (α1). Preferred water-dispersible monomers are acrylic acid esters and methacrylic acid esters, such as methyl(meth)acrylate, ethyl(meth)acrylate, propyl(meth)acrylate or butyl(meth)acrylate.

The monoethylenically unsaturated monomers (α2) which can be copolymerized with (α1) can also include methylpolyethylene glycol allyl ether, vinyl acetate, styrene and isobutylene.

Those compounds which are mentioned as crosslinking agents (α3) in WO 2004/037903 A2 are preferably employed as crosslinking agents (α3). Among these crosslinking agents, water-soluble crosslinking agents are particularly preferred. In this context, N,N'-methylenebisacrylamide, polyethylene glycol di(meth)acrylates, triallylmethylammonium chloride, tetraallylammonium chloride and allylnonaethylene glycol acrylate prepared with 9 mol of ethylene oxide per mol of acrylic acid are most preferred.

In addition to the monomers ($\alpha$1) and optionally ($\alpha$2) and optionally the crosslinking agent ($\alpha$3), the monomer solution can also comprise water-soluble polymers ($\alpha$4). Preferred water-soluble polymers ($\alpha$4) include partly or completely saponified polyvinyl alcohol, polyvinylpyrrolidone, starch or starch derivatives, polyglycols or polyacrylic acid. The molecular weight of these polymers is not critical, as long as they are water-soluble. Preferred water-soluble polymers ($\alpha$4) are starch or starch derivatives or polyvinyl alcohol. The water-soluble polymers ($\alpha$4), preferably synthetic, such as polyvinyl alcohol, can not only serve as a graft base for the monomers to be polymerized. It is also conceivable for these water-soluble polymers to be mixed with the polymer gel or the already dried, water-absorbing polymer gel only after the polymerization.

The monomer solution can furthermore also comprise auxiliary substances ($\alpha$5), these auxiliary substances including, in particular, the initiators which may be necessary for the polymerization, complexing agents, such as, for example, EDTA, and in particular also thermoplastic polymers or dispersions containing thermoplastic polymers.

Possible solvents for the monomer solution are water, organic solvents or mixtures of water and organic solvents, the choice of the solvent also depending in particular on the nature and method of the polymerization.

The relative amount of monomers ($\alpha$1) and ($\alpha$2) and of crosslinking agents ($\alpha$3) and water-soluble polymers ($\alpha$4) and auxiliary substances ($\alpha$5) in the monomer solution is preferably chosen such that the water-absorbing polymer structure obtained in process step iv) after drying is based

- to the extent of 20-99.999 wt. %, preferably to the extent of 55-98.99 wt. % and particularly preferably to the extent of 70-98.79 wt. % on monomers ($\alpha$1),
- to the extent of 0-80 wt. %, preferably to the extent of 0-44.99 wt. % and particularly preferably to the extent of 0.1-44.89 wt. % on the monomers ($\alpha$2),
- to the extent of 0-5 wt. %, preferably to the extent of 0.001-3 wt. % and particularly preferably to the extent of 0.01-2.5 wt. % on the crosslinking agents ($\alpha$3),
- to the extent of 0-30 wt. %, preferably to the extent of 0-5 wt. % and particularly preferably to the extent of 0.1-5 wt. % on the water-soluble polymers ($\alpha$4),
- to the extent of 0-20 wt. %, preferably to the extent of 0.10 wt. % and particularly preferably to the extent of 0.1-8 wt. % on the auxiliary substances ($\alpha$5), and
- to the extent of 0.5-25 wt. %, preferably to the extent of 1-10 wt. % and particularly preferably to the extent of 3-7 wt. % on water ($\alpha$6)

the sum of the amounts by weight ($\alpha$1) to ($\alpha$6) being 100 wt. %.

Optimum values for the concentration in particular of the monomers, crosslinking agents and water-soluble polymers in the monomer solution can be determined by simple preliminary experiments or from the prior art, in particular the publications U.S. Pat. No. 4,286,082, DE 27 06 135 A1, U.S. Pat. No. 4,076,663, DE 35 03 458 A1, DE 40 20 780 C1, DE 42 44 548 A1, DE 43 33 056 A1 and DE 44 18 818 A1.

In process step ii) of the process according to the invention, the aqueous monomer solution obtained in process step i) is subjected to free-radical polymerization to give a polymer gel, in principle all the polymerization processes known to the person skilled in the art being possible. For example, bulk polymerization, which is preferably carried out in kneading reactors, such as extruders, solution polymerization, spray polymerization, inverse emulsion polymerization and inverse suspension polymerization are to be mentioned in this connection.

The solution polymerization is preferably carried out in water as the solvent. The solution polymerization can be carried out continuously or discontinuously. A broad spectrum of possibilities of variation in respect of the reaction circumstances, such as temperatures, nature and amount of the initiators and also of the reaction solution, is to be found from the prior art. Typical processes are described in the following patent specifications: U.S. Pat. No. 4,286,082, DE 27 06 135 A1, U.S. Pat. No. 4,076,663, DE 35 03 458 A1, DE 40 20 780 C1, DE 42 44 548 A1, DE 43 33 056 A1 and DE 44 18 818 A1. The disclosures are introduced herewith as reference and therefore form part of the disclosure.

The polymerization is initiated by an initiator as is generally conventional. Initiators which can be used for initiation of the polymerization are all the initiators which form free radicals under the polymerization conditions and are conventionally employed in the preparation of superabsorbers. Initiation of the polymerization by the action of electron beams on the polymerizable aqueous mixture is also possible. Nevertheless, the polymerization can also be initiated in the absence of initiators of the abovementioned type by the action of high-energy radiation in the presence of photoinitiators. Polymerization initiators can be contained in dissolved or dispersed form in a solution of monomers according to the invention. Possible initiators are all the compounds known to the person skilled in the art which dissociate into free radicals. These include, in particular, those initiators which have already been mentioned as possible initiators in WO 2004/037903 A2.

A redox system comprising hydrogen peroxide, sodium peroxodisulphate and ascorbic acid is particularly preferably employed for preparation of the water-absorbing polymer structures.

Inverse suspension and emulsion polymerization can also be used in the process according to the invention. According to these processes, an aqueous, partly neutralized solution of monomers ($\alpha$1) and ($\alpha$2), optionally containing water-soluble polymers ($\alpha$4) and auxiliary substances ($\alpha$5), is dispersed in a hydrophobic organic solvent with the aid of protective colloids and/or emulsifiers and the polymerization is started by free radical initiators. The crosslinking agents ($\alpha$3) either are dissolved in the monomer solution and are metered together with this, or are added separately and optionally during the polymerization. The addition of a water-soluble polymer ($\alpha$4) as a graft base is optionally carried out via the monomer solution or by direct initial introduction into the oily phase. The water is then removed azeotropically from the mixture and the polymer is filtered off.

Both in the case of solution polymerization and in the case of inverse suspension and emulsion polymerization, the crosslinking can furthermore be carried out by polymerizing in the polyfunctional crosslinking agent ($\alpha$3) dissolved in the monomer solution and/or by reaction of suitable crosslinking agents with functional groups of the polymer during the polymerization steps. The processes are described, for example, in the publications U.S. Pat. No. 4,340,706, DE 37 13 601 A1, DE 28 40 010 A1 and WO 96/05234 A1, the corresponding disclosure of which is introduced herewith as reference.

In process step iii) of the process according to the invention, the polymer gel obtained in process step ii) is optionally comminuted, this comminution being carried out in particular if the polymerization is carried out by means of a solution polymerization. The comminution can be carried out by comminution devices known to the person skilled in the art, such as, for example, a mincing machine.

In process step iv) of the process according to the invention, the optionally previously comminuted polymer gel is dried. Drying of the polymer gel is preferably carried out in suitable dryers or ovens. Rotary tube ovens, fluidized bed dryers, plate dryers, paddle dryers or infrared dryers may be mentioned by way of example. It is furthermore preferable according to the invention for the drying of the polymer gel in process step iv) to be carried out down to a water content of from 0.5 to 25 wt. %, preferably from 1 to 10 wt. %, the drying temperatures conventionally being in a range of from 100 to 200° C.

In process step v) of the process according to the invention, the water-absorbing polymer structures obtained in process step iv) can be ground again, especially if they have been obtained by solution polymerization, and sieved to the above-mentioned desired grain size. The grinding of the dried, water-absorbing polymer structures is preferably carried out is suitable mechanical comminution devices, such as, for example, a ball mill, while the sieving can be carried out, for example, using sieves of suitable mesh width.

In process step vi) of the process according to the invention, the optionally ground and sieved water-absorbing polymer structures are post-crosslinked on the surface. For the surface post-crosslinking, the dried and optionally ground and sieved water-absorbing polymer structures from process step iv) or v), but the not yet dried but preferably already comminuted polymer gel from process step ii) or iii) is brought into contact with a preferably organic, chemical surface post-crosslinking agent. In this context, the post-crosslinking agent, especially if it is not liquid under the post-crosslinking conditions, is preferably brought into contact with the water-absorbing polymer structure or the polymer gel in the form of a fluid containing the post-crosslinking agent and a solvent. In this context, solvents which are employed are, preferably, water, water-miscible organic solvents, such as, for example, methanol, ethanol, 1-propanol, 2-propanol or 1-butanol, or mixtures of at least two of these solvents, water being most preferred as the solvent. It is furthermore preferable for the fluid to contain the post-crosslinking agent in an amount in a range of from 5 to 75 wt. %, particularly preferably 10 to 50 wt. % and most preferably 15 to 40 wt. %, based on the total weight of the fluid.

In the process according to the invention, the water-absorbing polymer structure or the optionally comminuted polymer gel is preferably brought into contact with the fluid containing the post-crosslinking agent by thorough mixing of the fluid with the polymer structure or the polymer gel.

Suitable mixing units for the application of the fluid are e.g. the Patterson-Kelley mixer, DRAIS turbulence mixer, Lödige mixer, Ruberg mixer, screw mixers, plate mixers and fluidized bed mixers and continuously operating vertical mixers, in which the polymer structure is mixed by means of rotating blades in rapid frequency (Schugi mixer).

In the process according to the invention, during the post-crosslinking the polymer structure or the polymer gel is preferably brought into contact with at most 20 wt. %, particularly preferably with at most 15 wt. %, moreover preferably with at most 10 wt. %, moreover even more preferably with at most 5 wt. % of solvent, preferably water.

In the case of polymer structures in the form of preferably spherical particles, it is furthermore preferable according to the invention for the bringing into contact to be effected merely by bringing the outer region, but not the inner region of the particulate polymer structure, into contact with the fluid and thus with the post-crosslinking agent.

Compounds which have at least two functional groups which can react with functional groups of a polymer structure in a condensation reaction (=condensation crosslinking agents), in an addition reaction or in a ring-opening reaction are preferably understood as post-crosslinking agents which are employed in the process according to the invention. Those post-crosslinking agents which have been mentioned as crosslinking agents of crosslinking agent class II in WO 2004/037903 A2 are preferred as post-crosslinking agents in the process according to the invention.

Among these compounds, particularly preferred post-crosslinking agents are condensation crosslinking agents, such as, for example, diethylene glycol, triethylene glycol, polyethylene glycol, glycerol, polyglycerol, propylene glycol, diethanolamine, triethanolamine, polyoxypropylene, oxyethylene/oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one(ethylene carbonate), 4-methyl-1,3-dioxolan-2-one(propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxolan-2-one.

After the polymer structures or the polymer gels have been brought into contact with the post-crosslinking agent or with the fluid containing the post-crosslinking agent, they are heated to a temperature in a range of from 50 to 300° C., preferably 75 to 275° C. and particularly preferably 150 to 250° C., so that preferably as a result the outer region of the polymer structure is more highly crosslinked compared with the inner region (=post-crosslinking), and if polymer gel is employed, this is dried at the same time. The duration of the heat treatment is limited by the risk that the desired profile of properties of the polymer structures is destroyed as a result of the action of heat.

In the process according to the invention, a thermoplastic polymer is added to

I) the aqueous monomer solution before process step ii) or during process step ii), preferably before process step ii), II) the polymer gel after process step ii) and before process step iv) or during process step iv), preferably before process step iv), or III) the water-absorbing polymer structure after process step iv).

According to particular embodiments of the process according to the invention, the thermoplastic polymer is added to (γ1) the aqueous monomer solution before process step ii), (γ2) the polymer gel before process step iv), (γ3) the water-absorbing polymer structure after process step iv), preferably before, during or after process step vi), (γ4) the aqueous monomer solution before process step ii) and the polymer gel before process step iv), (γ5) the aqueous monomer solution before process step ii) and the water-absorbing polymer structure after process step iv), preferably before, during or after process step vi), or (γ6) the polymer gel before process step iv) and the water-absorbing polymer structure after process step iv), preferably before, during or after process step vi), among these variants (γ1) and (γ3) being particularly preferred.

According to the invention, a "thermoplastic polymer" is preferably understood as meaning a polymer which can be shaped plastically by supplying heat. In this connection, according to the invention it is preferable for the thermoplastic polymer to have a melting or glass transition temperature, determined by dynamic differential calorimetry (DSC), in a range of from −100° C. to 200° C., particularly preferably −50 to 100° C. and most preferably −45 to 25° C.

Thermoplastic polymers which are preferred according to the invention are, in particular, polymers chosen from the group consisting of poly(meth)acrylates, (meth)acrylic acid co-polymers, for example ethylene/(meth)acrylic acid copolymer, (meth)acrylic acid ester co-polymers, maleic acid copolymers, for example maleic acid/propylene copolymers, polyurethanes, vinyl acetate copolymers, for example an ethylene/vinyl acetate copolymer or vinyl acetate/butyl acrylate copolymers, styrene copolymers, for example butyl acrylate/styrene copolymers, and polycarbonates. In this context, the term (meth)acrylic acid represents the two compounds methacrylic acid and acrylic acid, of these two acrylic acid being particularly preferred. Thermoplastic polymers which are preferred according to the invention as regards the chemical composition of the polymers are furthermore all those thermoplastic polymers which are mentioned as thermoplastic polymers in DE-A-103 34 286 and in WO-A-2005/044900. The disclosure content of DE-A-103 34 286 and WO-A-2005/044900 in respect of the thermoplastic polymers described there is introduced herewith as reference and forms a part of the disclosure of the present invention.

The number-average molecular weight ($M_n$), determined by gel permeation chromatography (GPC), of the thermoplastic polymers is, for example, between about 1,000 and about 10,000,000, between about 20,000 and about 1,000,000 or between about 50,000 and about 500,000 g/mol.

The molecular weight distribution of the polymers mentioned, as likewise can be determined by gel permeation chromatography (GPC), can be monomodal. A thermoplastic polymer can optionally also have a bimodal or polymodal distribution.

The abovementioned thermoplastic polymers can be employed in the process according to the invention as the pure substance, for example as polymer particles, or also in the form of a dispersion containing the thermoplastic polymer, a dispersion agent and optionally a dispersing agent, the use in the form of a dispersion being particularly preferred. In this context, the term "dispersion" is understood as meaning a mixture of the thermoplastic polymer and a dispersion agent, these two components not or scarcely dissolving in one another or bonding chemically to one another. In this context, the thermoplastic polymer is distributed as the dispersed phase (=disperse phase, "internal phase" or secondary phase) as finely as possible in the dispersion agent (=dispersant, continuous phase, "external phase" or main phase). Depending on whether the thermoplastic polymer is solid or liquid at the given temperature of the dispersion, the dispersion can be a suspension or also an emulsion.

In this context, dispersion agents which can be employed are, in particular, water, water-miscible organic solvents, such as, for example, methanol, ethanol, 1-propanol or 2-propanol, or mixtures of water and water-miscible organic solvents, the use of water as a dispersing agent being particularly preferred.

Dispersing agents which can be employed are all the compounds known to the person skilled in the art which enable the abovementioned thermoplastic polymers to be dispersed in water or in water-miscible organic solvents. Suitable dispersing agents are, for example, anionic, nonionic, cationic or amphoteric surface-active compounds, such as, for example, fatty acid salts, coco-amines, coco-amides and their salts, salts of sulphuric acid alkyl esters, salts of alkylbenzenesulphonic acid, dialkylsulphosuccinates, alkyl phosphate salts and polyoxyethylene alkyl sulphate salts, polyoxyethylene alkyl ethers, polyoxyethylene alkyl-phenol ethers, ethoxylated alcohols, propoxylated alcohols, amino alcohols, polyoxyethylene fatty acid esters, sorbitan fatty acid esters, polyoxysorbitan fatty aced esters, polyoxyethylenealkylamines, fatty acid esters, oxyethylene/oxypropylene block polymers, salts of alkylamines, quaternary ammonium salts and lauryldimethylamine oxides. Such surface-active substances can be employed for the preparation of the dispersions individually or in combination with one another.

In this connection, it is furthermore preferable for the dispersion containing the thermoplastic polymer, the dispersion agent and optionally the dispersing agent to have a Brookfield viscosity, determined at 20° C., in a range of from 0.1 to 10,000 mPa×sec, particularly preferably in a range of from 1 to 5,000 mPa-sec and most preferably in a range of from 5 to 3,000 mPa-sec.

It is furthermore preferable according to the invention for the dispersion to contain the thermoplastic polymer in an amount in a range of from 5 to 95 wt. %, particularly preferably in a range of from 20 to 80 wt. %, moreover preferably in a range of from 30 to 70 wt. % and most preferably in a range of from 40 to 60 wt. %, in each case based on the total weight of the dispersion.

Polymer dispersions which are suitable according to the invention are, for example, the dispersions obtainable under the name Lurapret® (BASF AG, Ludwigshafen), such as, for example, the products Lurapret®DPC, Lurapret®DPH, Lurapret®D 312, Lurapret®D 456 or Lurapret®D 500, the dispersion obtainable from the company Alberdingk Boley GmbH in Krefeld under the names AC 31, AC 2538, AC 2511, AC 2039, AC 7574, AC 75012, AC 75030 and AC 75036, the dispersion obtainable from the company Ruderer Klebetechnik GmbH in Zorneding under the name Ruderer 2038, or the products obtainable under the name Airflex® from the company Air Products, Allentown, USA, such as, for example, Air-flex®315.

If the thermoplastic polymer is added to the aqueous monomer solution in the process according to the invention according to alternative I) before process step ii) or during process step ii), it is furthermore preferable for the thermoplastic polymer to be added to the monomer solution in an amount in a range of from 0.01 to 10 wt. %, preferably in a range of from 0.05 to 5 wt. % and most preferably in an amount in a range of from 0.1 to 1 wt. %, in each case based on the total weight of the monomer solution. If the thermoplastic polymer is employed in the form of the dispersion described above, the abovementioned amounts data are to be related to the solids content of the dispersion.

If the thermoplastic polymer is added to the polymer gel in the process according to the invention after process step ii) and before process step iv) or during process step iv) or to the water-absorbing polymer structure after process step iv) according to alternatives II) and III), preferably to the water-absorbing polymer structure after process step iv) according to alternative III), it is furthermore preferable for the thermoplastic polymers to be added in an amount in a range of from 0.001 to 5 wt. %, preferably in range of from 0.01 to 1 wt. % and most preferably in an amount in a range of from 0.05 to 0.5 wt. %, in each case based on the total weight of the polymer gel or of the water-absorbing polymer structure. Here also, in the case of the use of the polymer dispersion described above, the amounts data are to be related to the solids content of the polymer dispersion.

If the thermoplastic polymer or the dispersion containing the thermoplastic polymer is added to the monomer solution in accordance with alternative I), the thermoplastic polymer or the dispersion can be fed to the reaction mixture in a simple manner before, during or after the addition of the monomers. If the addition of the thermoplastic polymer or of the dispersion to the polymer gel takes place before process step iv), the thermoplastic polymer or the dispersion in incorporated in a simple manner into the polymer gel obtained in process step ii) and/or into the comminuted polymer gel optionally obtained in process step iii) by means of suitable kneading devices, for example by mincing the polymer gel in the presence of the thermoplastic polymer or the dispersion.

On the other hand, if the thermoplastic polymer or the dispersion is added to the water-absorbing polymer structure after process step iv) in accordance with alternative III), it is particularly preferable for the thermoplastic polymer or the dispersion to be brought into contact with the water-absorbing polymer structure before, during or after the surface crosslinking in process step vi). In this context, the following variants are conceivable:

- δ1) the water-absorbing polymer structure which has been obtained in process step vi) or v) is first brought into contact with the thermoplastic polymer or the dispersion and the fluid containing the post-crosslinking agent and the mixture is then heated to the required post-crosslinking temperature, it being possible for the thermoplastic polymer or the dispersion and the fluid containing the post-crosslinking agent to be employed separately from one another or in the form of a common fluid;
- δ2) the water-absorbing polymer structure which has been obtained in process step vi) or v) is first brought into contact with the fluid containing the post-crosslinking agent and the mixture is then heated to the required post-crosslinking temperature, the thermoplastic polymer or the dispersion being added during the heating;
- δ3) the water-absorbing polymer structure which has been obtained in process step vi) or v) is first brought into contact with the fluid containing the post-crosslinking agent and the mixture is then heated to the required post-crosslinking temperature, and only when the post-crosslinking reaction has ended, for example during make-up, is the thermoplastic polymer or the dispersion added, it optionally being possible, after addition of the thermoplastic polymer or the dispersion, for the water-absorbing polymer obtained in this way to be heated further, preferably to a temperature above the melting or glass transition temperature of the thermoplastic polymer.

It may furthermore be advantageous for still further surface modifications, such as, for example, coating of the surface post-crosslinked water-absorbing polymer structures with socalled "anti-caking" agents, with flow auxiliaries, such as, for example, polyethylene glycols, with odor-binding agents, such as, for example, cyclodextrins or zeolites, or with permeability-increasing agents, to be carried out after process step vi).

According to a particularly preferred embodiment, however, after process step iv) the surface of the water-absorbing polymer structures is brought into contact with less than 5 wt. %, preferably less than 1 wt. %, particularly preferably less than 0.1 wt. %, even more preferably less than 0.01 wt. %, in each case based on the weight of the water-absorbing polymer structures, of a very fine particle, preferably an inorganic or organic powder, particularly preferably an inorganic powder and most preferably an SiO compound, it being most preferable for the water-absorbing polymer structures no longer to be brought into contact at all with a vary fine particle, preferably no longer with an inorganic or organic powder, even more preferably no longer with an inorganic powder and most particularly preferably no longer with an SiO compound. This applies in particular if the thermoplastic polymer or the dispersion has been added to the water-absorbing polymer structure after process step iv), preferably before, during or after process step vi). Surprisingly, it has been found, in fact, that by using in particular dispersions containing thermoplastic polymers with the monomer solution or also with the water-absorbing polymer structure, absorbent products which have excellent permeabilities and flow properties even without an addition of very fine particles, in particular without the addition of inorganic powders, but at least by addition of significantly lower amounts of inorganic powders, compared with the prior art, as permeability-increasing agents or as agents for improving flowability, can be obtained. The wording "brought into contact with less than 5 wt. %, preferably less than 1 wt. %, particularly preferably less than 0.1 wt. %, even more preferably less than 0.01 wt. % and most preferably no longer at all with a fine particle after process step iv)" in this context means that after the drying, very fine particles are no longer employed, whether before, during or after the surface post-crosslinking, and in particular neither as a pure powder nor as a fluid, for example as a suspension, containing the very fine particle and a solvent. According to another embodiment of the process according to the invention, also less than 5 wt. %, preferably less than 1 wt. %, particularly preferably less than 0.1 wt. %, even more preferably less than 0.01 wt. %, in each case based on the weight of the monomer solution, and most preferably no fine particles at all, preferably no inorganic or organic powder, most preferably no inorganic powder, are added to the monomer solution.

"Very fine particles" which are preferably employed in the abovementioned maximum amounts or most preferably are not employed at all are preferably understood as meaning those very fine particles which have been mentioned as very fine particles in DE 103 34 286, the chemical composition of the very fine particles preferably differing from the chemical composition of the water-absorbing polymer structures. The very fine particles preferably have a particle size, determine by sieve analysis, of less than 200 μm, particularly preferably of less than 100 μm and most preferably of less than 50 μm.

A contribution to achieving the abovementioned objects is also achieved by a water-absorbing polymer structure which is obtainable by the process according to the invention described above. In this context, it is particularly preferable for the water-absorbing polymer structure according to the invention to comprise monomers carrying carboxylate groups to the extent of at least 50 wt. %, preferably to the extent of at least 70 wt. % and moreover preferably to the extent of at least 90 wt. %, in each case based on the weight of the water-absorbing polymer structure. It is further preferable according to the invention for the water-absorbing polymer structure according to the invention to be based to the extent of at least 50 wt. %, preferably to the extent of at least 70 wt. %, in each case based on the weight of the water-absorbing polymer structure, on polymerized acrylic acid, which is preferably neutralized to the extent of at least 20 mol %, particularly preferably the to extent of at least 50 mol % and moreover preferably in a range of from 60 to 85 mol %.

It is furthermore preferable according to the invention for the water-absorbing polymer structure obtainable by the process according to the invention to be characterized by at least one of the, but preferably all the following properties:

- (β1) a dust content, determined in accordance with the test method described herein for the total particle fraction, of not more than 2%, preferably not more than 1.5%, even more preferably not more than 1%, moreover preferably not more than 0.5%, moreover even more preferably not more than 0.3%;
(β2) a flow value, determined in accordance with the test method described herein for the total particle fraction, of not more than 15, preferably not more than 10, even more preferably not more than 7.5, the flow value preferably being at least 5, particularly preferably at least 5.5;
(β3) at a retention of <25 g/g, determined in accordance with ERT 441.2-02, a gel bed permeability (GBP), determined in accordance with the test method described herein, of at least 50 Darcy, preferably at least 100 Darcy and most preferably at least 150 Darcy;
(β4) at a retention of ≥25 g/g and <27 g/g, determined in accordance with ERT 441.2-02, a gel bed permeability (GBP), determined in accordance with the test method described herein, of at least 45 Darcy, preferably at least 90 Darcy and most preferably at least 120 Darcy;
(β5) at a retention of ≥27 g/g and <29 g/g, determined in accordance with ERT 441.2-02, a gel bed permeability (GBP), determined in accordance with the test method described herein, of at least 40 Darcy, preferably at least 70 Darcy and most preferably at least 100 Darcy;
(β6) at a retention of ≥29 g/g and <31 g/g, determined in accordance with ERT 441.2-02, a gel bed permeability (GBP), determined in accordance with the test method described herein, of at least 30 Darcy, preferably at least 45 Darcy and most preferably at least 60 Darcy;
(β7) at a retention of ≥31 g/g and <33 g/g, determined in accordance with ERT 441.2-02, a gel bed permeability (GBP), determined in accordance with the test method described herein, of at least 20 Darcy, preferably at least 30 Darcy and most preferably at least 40 Darcy;
(β8) at a retention of ≥33 g/g and <35 g/g, determined in accordance with ERT 441.2-02, a gel bed permeability (GBP), determined in accordance with the test method described herein, of at least 15 Darcy, preferably at least 20 Darcy and most preferably at least 25 Darcy;
(β9) at a retention of ≥35 g/g, determined in accordance with ERT 441.2-02, a gel bed permeability (GBP), determined in accordance with the test method described herein, of at least 8 Darcy, preferably at least 10 Darcy and most preferably at least 15 Darcy.

Embodiments of the water-absorbing polymer structures obtainable by the process according to the invention which are furthermore preferred have any conceivable combination of the above features (β1) to (β9), the embodiments of the following combinations of features being preferred: (β1), (β2), (β3), (β4), (β5), (β6), (β7), (β8), (β9), (β1)(β2), (β3) (β4)(β5)(β6)(β7)(β8)(β9), (β1)(β3)(β4)(β5)(β6)(β7)-(β8) (β9) and (β1)(β2)(β3)(β4)(β5)(β6)(β7)(β8)(β9), (β1)(β2) (β3)(β4)(β5)(β6)(β7)(β8)(β9) being the most preferred combinations of properties.

The present invention also relates to a water-absorbing polymer structure which has at least one of the following properties:
(β1) a dust content, determined in accordance with the test method described herein for the total particle fraction, of not more than 2%, preferably not more than 1.5%, even more preferably not more than 1%, moreover preferably not more than 0.5%, moreover even more preferably not more than 0.3%;
(β2) a flow value, determined in accordance with the test method described herein for the total particle fraction, of not more than 15, preferably not more than 10, even more preferably not more than 7.5, the flow value preferably being at least 5, particularly preferably at least 5.5;
(β3) at a retention of <25 g/g, determined in accordance with ERT 441.2-02, a gel bed permeability (GBP), determined in accordance with the test method described herein, of at least 50 Darcy, preferably at least 100 Darcy and most preferably at least 150 Darcy;
(β4) at a retention of ≥25 g/g and <27 g/g, determined in accordance with ERT 441.2-02, a gel bed permeability (GBP), determined in accordance with the test method described herein, of at least 45 Darcy, preferably at least 90 Darcy and most preferably at least 120 Darcy;
(β5) at a retention of ≥27 g/g and <29 g/g, determined in accordance with ERT 441.2-02, a gel bed permeability (GBP), determined in accordance with the test method described herein, of at least 40 Darcy, preferably at least 70 Darcy and most preferably at least 100 Darcy;
(β6) at a retention of ≥29 g/g and <31 g/g, determined in accordance with ERT 441.2-02, a gel bed permeability (GBP), determined in accordance with the test method described herein, of at least 30 Darcy, preferably at least 45 Darcy and most preferably at least 60 Darcy;
(β7) at a retention of ≥31 g/g and <33 g/g, determined in accordance with ERT 441.2-02, a gel bed permeability (GBP), determined in accordance with the test method described herein, of at least 20 Darcy, preferably at least 30 Darcy and most preferably at least 40 Darcy;
(β8) at a retention of ≥33 g/g and <35 g/g, determined in accordance with ERT 441.2-02, a gel bed permeability (GBP), determined in accordance with the test method described herein, of at least 15 Darcy, preferably at least 20 Darcy and most preferably at least 25 Darcy;
(β9) at a retention of ≥35 g/g, determined in accordance with ERT 441.2-02, a gel bed permeability (GBP), determined in accordance with the test method described herein, of at least 8 Darcy, preferably at least 10 Darcy and most preferably at least 15 Darcy.

In this context, it is preferable for the water-absorbing polymer structure according to the invention to have the same properties as the water-absorbing polymer structure obtainable by the process according to the invention. It is also preferable according to the invention for those values which have been stated in connection with the process according to the invention and the water-absorbing polymer structures according to the invention as lower limits of features according to the invention without upper limits to have 20 times, preferably 10 times and particularly preferably 5 times the most preferred value of the lower limit.

According to a particular embodiment of the water-absorbing polymer structure according to the invention and of the water-absorbing polymer structure obtainable by the process according to the invention, this polymer structure comprises less than 5 wt. %, preferably less than 1 wt. %, particularly preferably less than 0.1 wt. %, even more preferably less than 0.01 wt. % of a very fine particle, preferably an inorganic or organic powder, particularly preferably an inorganic powder and most preferably an SiO compound, it being most preferable for the water-absorbing polymer structure to contain no fine particle at all, preferably no inorganic or organic power at all, particularly preferably no inorganic powder at all, most preferably no SiO compound at all.

A further contribution to achieving the objects described above is made by a composite material comprising the water-absorbing polymer structures according to the invention or the water-absorbing polymer structures obtainable by the process according to the invention and a substrate. In this context, it is preferable for the water-absorbing polymer structures according to the invention and the substrate to be firmly bonded to one another. Preferred substrates are films of polymers, such as, for example, of polyethylene, polypropylene or polyamide, metals, nonwovens, fluff, tissues, woven fabric, natural or synthetic fibers, or other foams. It is furthermore preferable according to the invention for the composite material to include at least one region which comprises the water-absorbing polymer structure according to the invention in an amount in the range of from about 15 to 100 wt. %, preferably about 30 to 100 wt. %, particularly preferably from about 50 to 99.99 wt. %, furthermore preferably from about 60 to 99.99 wt. % and moreover preferably from about 70 to 99 wt. %, in each case based on the total weight of the composite material region in question, this region preferably having a size of at least 0.01 cm$^3$, preferably at least 0.1 cm$^3$ and most preferably at least 0.5 cm$^3$.

In a particularly preferred embodiment of the composite material according to the invention, this is a planar composite material such as is described as "absorbent material" in WO 02/056812 A1. The disclosure content of WO 02/056812 A1, in particular with respect to the precise structure of the composite material, the weight per unit area of its constituents and its thickness, is introduced herewith as reference and represents a part of the disclosure of the present invention.

A further contribution to achieving the abovementioned objects is made by a process for the production of a composite material, wherein the water-absorbing polymer structures according to the invention or the water-absorbing polymer structures obtainable by the process according to the invention and a substrate and optionally an additive are brought into contact with one another. Substrates which are employed are preferably those substrates which have already been mentioned above in connection with the composite material according to the invention.

A contribution to achieving the abovementioned objects is also made by a composite material obtainable by the process described above, this composite material preferably having the same properties as the composite material according to the invention described above.

A further contribution to achieving the abovementioned objects is made by chemical products comprising the polymer structures according to the invention or a composite material according to the invention. Preferred chemical products are, in particular, foams, shaped articles, fibers, foils, films, cables, sealing materials, liquid-absorbing hygiene articles, in particular diapers and sanitary towels, carriers for plant or fungal growth-regulating agents or plant protection active compounds, additives for building materials, packaging materials or soil additives.

The use of the polymer structures according to the invention or of the composite material according to the invention in chemical products, preferably in the abovementioned chemical products, in particular in hygiene articles, such as diapers or sanitary towels, and the use of the superabsorber particles as carriers for plant or fungal growth-regulating agents or plant protection active compounds also make a contribution to achieving the abovementioned objects. In the use as a carrier for plant or fungal growth-regulating agents or plant protection active compounds, it is preferable for the plant or fungal growth-regulating agents or plant protection active compounds to be able to be released over a period of time controlled by the carrier.

A further contribution to achieving the abovementioned object is made by the use of thermoplastic polymer, preferably in the form of a dispersion containing the thermoplastic polymer, a dispersion agent and optionally a dispersing agent, as described above, as an additive for the monomer solution described above or as a surface-modifying agent for water-absorbing polymer structures.

The invention will now be explained in more details with the aid of FIGURES, test methods and non-limiting examples.

FIGURES

FIG. 1 shows the influence of increasing amounts of the thermoplastic polymer dispersion Lurapret®D313 on the retention and on the permeability on addition of this polymer dispersion to the post-crosslinking agent solution.

Test Methods

Determination of the Flow Value (FFC Value)

The FFC value provides information on the flow properties of bulk goods in a silo. For the measurement, the bulk goods are exposed to various loads. The flow properties can be characterized as follows:

FFC<1 non-flowing
1<FFC<2 very cohesive
2<FFC<4 cohesive
4<FFC<10 readily flowing
10<FFC free-flowing Good flow properties exist if bulk goods can be made to flow without great effort, e.g. the bulk goods flow out of a hopper or a silo without consolidation. In the case of poorly flowing bulk goods, disturbances in the outflow occur, or they undergo consolidation during transportation or storage. The term "flow" means that the bulk goods deform plastically under load.

Further information on the precise procedure of the test for determination of the FFC is to be found in the articles by Dr. Ing. Dietmar Schulze "Das automatische Ringschergerät RST-01.pc [The automatic ring shear tester RST-01.pc]" from February 2002 and "Fließeigen-schaften von Schüttgütern and verfahrenstechnische Siloauslegung [Flow properties of bulk goods and process technology silo design]" from 2002. The manually operated variant of the ring shear tester RST-01.01 was used for the present measurements.

Determination of the Dust Content

The dust content is determined with an apparatus from the company Palas, Germany of the type "Dust View". For this, a sample of 30.00 g is introduced into a funnel tube. At the start of the measurement a funnel flap opens automatically and the sample falls into a dust reservoir. The reduction in a laser beam (decrease in transmission) due to the formation of dust is now measured. This values serves for determination of the dust content, i.e. the clouding, in per cent with a scale of from 1 to 100. The dust content is obtained from a starting value at the start of the measurement and a dust value measured after 30 seconds for determination of the suspended content. The dust content thus results from the sum of the starting value and the dust value.

Determination of the Gel Bed Permeability

The gel bed permeability is determined by the test method disclosed in U.S. Pat. No. 6,387,495 B1, the determination being carried out under atmospheric pressure and not under atmospheric pressure+0.3 psi as described in U.S. Pat. No. 6,387,495 B1.

EXAMPLES

Production of the Water-Absorbing Polymer Structure

A monomer solution containing 600 g acrylic acid, which was neutralized to the extent of 70 mol % with sodium hydroxide solution (466.22 g, 50% strength NaOH), 900.26 g water, 1.44 g polyethylene glycol 300 diacrylate and 1.44 g monoallyl polyethylene glycol 450 monoacrylic acid ester is freed from dissolved oxygen by flushing with nitrogen and cooled to the start temperature of 4° C. When the start temperature was reached, the initiator solution (0.6 g sodium peroxydisulphate in 10 g $H_2O$, 0.014 g 35% strength hydrogen peroxide solution in 10 g $H_2O$ and 0.03 g ascorbic acid in 10 g $H_2O$) was added. When the end temperature of approx. 100° C. was reached, the gel formed was comminuted with a meat mincer and dried at 150° C. in a drying cabinet for 2 hours. The dried polymer was coarsely crushed, ground by means of a ring-beater mill (company Retsch ZM1) with a 5 mm sieve and sieved to a powder having a particle size of from 150 to 850 µm.

Post-Crosslinking 100 g of the powder are mixed with a post-crosslinking solution containing 1.0 g ethylene carbonate and 3 g deionized water by means of a vertical mixer (MTI-Mischtechnik Industrieanlagen GmbH, type LM 1.5/5), the solution being applied to the polymer powder in a mixer by means of a syringe with a 0.45 mm cannula. The powder A coated with the aqueous solution was then heated at 185° C. in a circulating air cabinet for 30 minutes. The water-absorbing polymer powder B is obtained (comparison polymer).

Example 1

Addition of a Polymer Dispersion to the Monomer Solution

The preparation example is repeated, 1 wt. %, based on the amount of acrylic acid in the monomer solution, of the thermoplastic polymer emulsion Lurapret®456 (based on the solids content) being added to the monomer solution. The water-absorbing polymer powder C is obtained.

Example 2

Addition of a Polymer Dispersion to the Monomer Solution

The preparation example is repeated, 1 wt. %, based on the amount of acrylic acid in the monomer solution, of the thermoplastic polymer emulsion Lurapret®DPS (based on the solids content) being added to the monomer solution. The water-absorbing polymer powder D is obtained.

Example 3

Addition of a Polymer Dispersion to the Monomer Solution

The preparation example is repeated, 0.5 wt. %, 0.75 wt. %, 1.0 wt. % or 1.5 wt. %, in each case based on the amount of acrylic acid in the monomer solution, of the thermoplastic polymer emulsion Airflex 315 being added to the monomer solution. The water-absorbing polymer powders E, F, G and H are obtained.

Example 4

Addition of a Polymer Dispersion to the Monomer Solution

The preparation example is repeated, 1.0 wt. %, based on the amount of acrylic acid in the monomer solution, of the thermoplastic polymer emulsion ALBERDINGK®AC 7502 (based on the solids content) being added to the monomer solution. The water-absorbing polymer powder I is obtained.

The properties of the polymer powders B to I are shown in the following Table 1:

TABLE 1

| Polymer powder | Retention [g/g] | GBP [Darcy] |
|---|---|---|
| B | 28.4 | 14.0 |
| C | 29.0 | 90.8 |
| D | 29.0 | 94.5 |
| E | 28.6 | 74.8 |
| F | 28.7 | 79.9 |
| G | 28.3 | 107.2 |
| H | 28.4 | 113.3 |
| I | 28.0 | 126.6 |

It can be seen from Table 1 that the addition of thermoplastic polymers to the monomer solution leads to a significant increase in the permeability with the retention remaining about the same.

Example 5

Addition of a Polymer Dispersion During the Post-Crosslinking

The preparation example is repeated, the thermoplastic polymer emulsion ALBERDINGK®AC 2538 being added to the post-crosslinking agent solution in an amount such that powder A is brought into contact with 1,000 ppm of the polymer dispersion. The water-absorbing polymer powder J is obtained.

Example 6

Addition of a Polymer Dispersion During the Post-Crosslinking

The preparation example is repeated, the thermoplastic polymer emulsion ALBERDINGK®AC 75030 being added to the post-crosslinking agent solution in an amount such that powder A is brought into contact with 1,000 ppm of the polymer dispersion. The water-absorbing polymer powder K is obtained.

Example 7

Addition of a Polymer Dispersion During the Post-Crosslinking

The preparation example is repeated, the thermoplastic polymer emulsion ALBERDINGK®AC 75036 being added to the post-crosslinking agent solution in an amount such that powder A is brought into contact with 1,000 ppm of the polymer dispersion. The water-absorbing polymer powder L is obtained.

Example 8

Addition of a Polymer Dispersion During the Post-Crosslinking

The preparation example is repeated, the thermoplastic polymer emulsion Lurapret®D313 being added to the post-crosslinking agent solution in an amount such that powder A is brought into contact with 3,000 ppm of the polymer dispersion (based on the solids content). The water-absorbing polymer powder M is obtained. In further experiments, the thermoplastic powder was also added in amounts such that powder A is brought into contact with 100 ppm, 300 ppm, 500 ppm, 1,000 ppm and 5,000 ppm of the polymer dispersion. The result can be seen from FIG. 1.

Example 9

Addition of a Polymer Dispersion During the Post-Crosslinking

The preparation example is repeated, the thermoplastic polymer emulsion Lurapret®D500 being added to the post-crosslinking agent solution in an amount such that powder A is brought into contact with 1,000 ppm of the polymer dispersion (based on the solids content). The water-absorbing polymer powder N is obtained.

The properties of polymer powders B and J to N are shown in the following Table 2:

TABLE 2

| Polymer powder | Retention [g/g] | GBP [Darcy] | Dust content [%] |
|---|---|---|---|
| B | 28.4 | 14.0 | n.d. |
| J | 29.3 | 75.5 | 0.13 |
| K | 28.9 | 96.0 | 0.00 |
| L | 29.7 | 92.7 | 0.20 |
| M | 28.5 | 103.1 | n.d. |
| N | 28.4 | 100.5 | n.d. |

It can be seen from Table 2 that the addition of thermoplastic polymers during the post-crosslinking leads to a significant increase in the permeability with the retention remaining about the same even without the addition of inorganic very fine particles, such as, for example, SiO powders. It can be seen from FIG. 1 that as the amount of thermoplastic polymer increases, the permeability increases. Since no very fine particles have to be employed to achieve a good permeability, water-absorbing powders having a particularly low dust content can be obtained.

The invention claimed is:

1. A process for producing water-absorbing polymer structures, comprising the process steps of:
   i) providing an aqueous monomer solution comprising
      from 70 to 98.79 wt % of a polymerizable, monoethylenically unsaturated monomer ($\alpha 1$) bearing acid groups, or a salt thereof,
      from 0.01 to 2.5 wt % of a crosslinker ($\alpha 3$), and
      adding from 0.05 to 5 wt % based on the total weight of the monomer solution of a thermoplastic polymer dispersion having a Brookfield viscosity in a range of from 5 to 3,000 mPa·sec, determined at 20° C., to the aqueous monomer solution and wherein the thermoplastic polymer dispersion is a mixture of the thermoplastic polymer and a dispersion agent wherein these two components do not dissolve in one another,
   ii) free-radically polymerizing the aqueous monomer solution to obtain a polymer gel,
   iii) comminuting the polymer gel to form comminuted polymer gel,
   iv) drying the comminuted polymer gel of step iii) to obtain water-absorbing polymer structures,
   v) grinding and sieving the water-absorbing polymer structures, and
   vi) surface postcrosslinking the ground and sieved water-absorbing polymer structures of step v),
   wherein the thermoplastic polymer dispersion is added to the aqueous monomer solution before process step ii) or during process step ii) and wherein the water-absorbing polymer structures do not contain a silicon oxide compound and wherein the water-absorbing polymer structures have the following properties:
   ($\beta 1$) a dust content determined by the test method described herein for the entire particle fraction of not more than 1.0%
   ($\beta 2$) a flow value determined by the test method described herein for the entire particle fraction of at most about 15;
   ($\beta 3$) a retention, as determined according to ERT 441.2-02, of from about 25 g/g to about 35 g/g;
   ($\beta 4$) a Gel Bed Permeability, as determined by the test method described herein, of from about 30 darcy to about 150 darcy wherein the value of the Gel Bed Permeability increases from 74.8 darcy to 113.3 darcy when the amount of thermoplastic polymer dispersion is increased from 0.5 wt % to 1.5 wt %; and
   ($\beta 5$) at least 50 wt. % based on the total weight of the post crosslinked water-absorbing polymer structures having a particle size in a range of from 300 to 600 μm.

2. The process as claimed in claim 1, wherein the thermoplastic polymer dispersion is added to the aqueous monomer solution before process step ii).

3. The process as claimed in claim 1 wherein the thermoplastic polymer has a melting temperature or glass transition temperature determined by ISO 11357 within a range from about −100° C. to about 200° C.

4. The process as claimed claim 1 wherein the thermoplastic polymer is used in the form of a dispersion comprising the thermoplastic polymer, a dispersion medium and optionally a dispersant.

5. The process as claimed in claim 4 wherein, when the dispersion is added to the aqueous monomer solution before process step ii), the dispersion is added to the monomer solution in an amount within a range from about 0.05 to about 5% by weight, based on the total weight of the monomer solution.

6. The process as claimed in claim 1 wherein the thermoplastic polymer is a polyacrylate, a (meth)acrylic acid copolymer, an ethylene-(meth)acrylic acid copolymer, a (meth)acrylic ester copolymer, a maleic acid copolymer, a maleic acid-propylene copolymer, a polyurethane, a vinyl acetate copolymer, an ethylene-vinyl acetate copolymer or a vinyl acetate-butyl acrylate copolymer, a styrene copolymer, a butyl acrylate-styrene copolymer, or a polycarbonate.

7. The process as claimed in claim 4 wherein the dispersion medium is water.

8. The process as claimed in claim 4 wherein the amount of thermoplastic polymer in the dispersion is within a range from about 5 to about 95% by weight, based on the total weight of the dispersion.

9. A process for producing water-absorbing polymer structures, comprising the process steps of:
   i) providing an aqueous monomer solution comprising
      a polymerizable, monoethylenically unsaturated monomer ($\alpha 1$) bearing acid groups, or a salt thereof,
      a crosslinker ($\alpha 3$), and
      a thermoplastic polymer dispersion having a Brookfield viscosity in a range of from 5 to 3,000 mPa·sec, determined at 20° C. and wherein the thermoplastic polymer dispersion is a mixture of the thermoplastic polymer and a dispersion agent wherein these two components do not dissolve in one another;
   ii) free-radically polymerizing the aqueous monomer solution to obtain a polymer gel, iii) comminuting the polymer gel to form comminuted polymer gel,
iv) drying the comminuted polymer gel to obtain water-absorbing polymer structures,
v) grinding and sieving the water-absorbing polymer structures, and
vi) surface postcrosslinking the ground and sieved water-absorbing polymer structures of step v),
wherein the thermoplastic polymer dispersion is added to the aqueous monomer solution before process step ii) or during process step ii) and wherein the water-absorbing polymer structures do not contain a silicon oxide compound and wherein the water-absorbing polymer structures have the following properties:
($\beta$1) a dust content determined by the test method described herein for the entire particle fraction of not more than 1.0%;
($\beta$2) a flow value determined by the test method described herein for the entire particle fraction of at most about 15;
($\beta$3) a retention as determined according to ERT 441.2-02 of from about 25 g/g to about 35 g/g; and
($\beta$4) a Gel Bed Permeability determined by the test method described herein of from about 30 darcy to about 150 darcy wherein the value of the Gel Bed Permeability increases from 74.8 darcy to 113.3 darcy when the amount of thermoplastic polymer dispersion is increased from 0.5 wt % to 1.5 wt %.

* * * * *